United States Patent [19]

Maniglia

[11] Patent Number: 5,015,224
[45] Date of Patent: May 14, 1991

[54] PARTIALLY IMPLANTABLE HEARING AID DEVICE

[76] Inventor: Anthony J. Maniglia, 14450 County Line Rd., Hunting Valley, Ohio 44022

[21] Appl. No.: 568,841

[22] Filed: Aug. 17, 1990

Related U.S. Application Data

[62] Division of Ser. No. 258,788, Oct. 17, 1988, Pat. No. 4,957,478.

[51] Int. Cl.⁵ .......................................... H04R 25/00
[52] U.S. Cl. ....................................... 600/25; 623/10; 128/419 R
[58] Field of Search ............... 623/10, 11, 16; 600/25; 128/419 R

[56] References Cited

U.S. PATENT DOCUMENTS

| | | | |
|---|---|---|---|
| 3,752,939 | 8/1973 | Bartz | 600/25 X |
| 3,764,748 | 10/1973 | Branch et al. | 600/25 X |
| 4,606,329 | 8/1986 | Hough | 600/25 |
| 4,800,884 | 1/1989 | Heide et al. | 128/419 R |
| 4,850,962 | 7/1989 | Schaefer | 600/25 |

Primary Examiner—Richard J. Apley
Assistant Examiner—Joe H. Cheng

[57] ABSTRACT

Partially implantable hearing device having easily replaceable components. Outer ear canal units contain the microphone, power source and electronics for receiving acoustic energy or sound waves and converting them into a responsive and variable magnetic field. Magnetic fields of magnets implanted onto bones in the ossicular chain in the ear interact with the variable magnetic field to cause the bones in the ossicular chain to vibrate in response to received sound waves. The variable magnetic field can be created directly via electrical signals or indirectly wherein intermediate radio frequency waves are transmitted and received between external and implanted components.

20 Claims, 13 Drawing Sheets

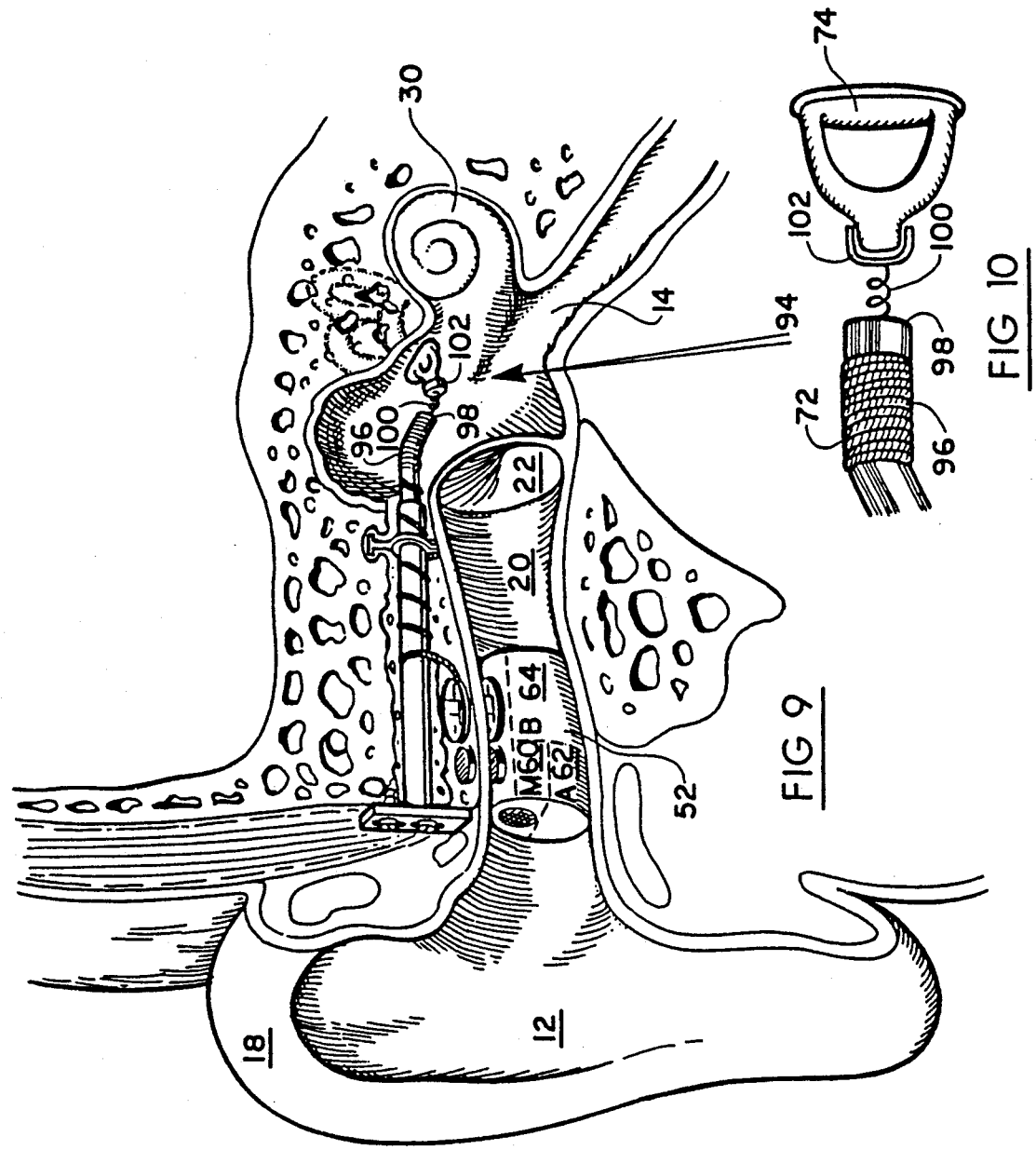

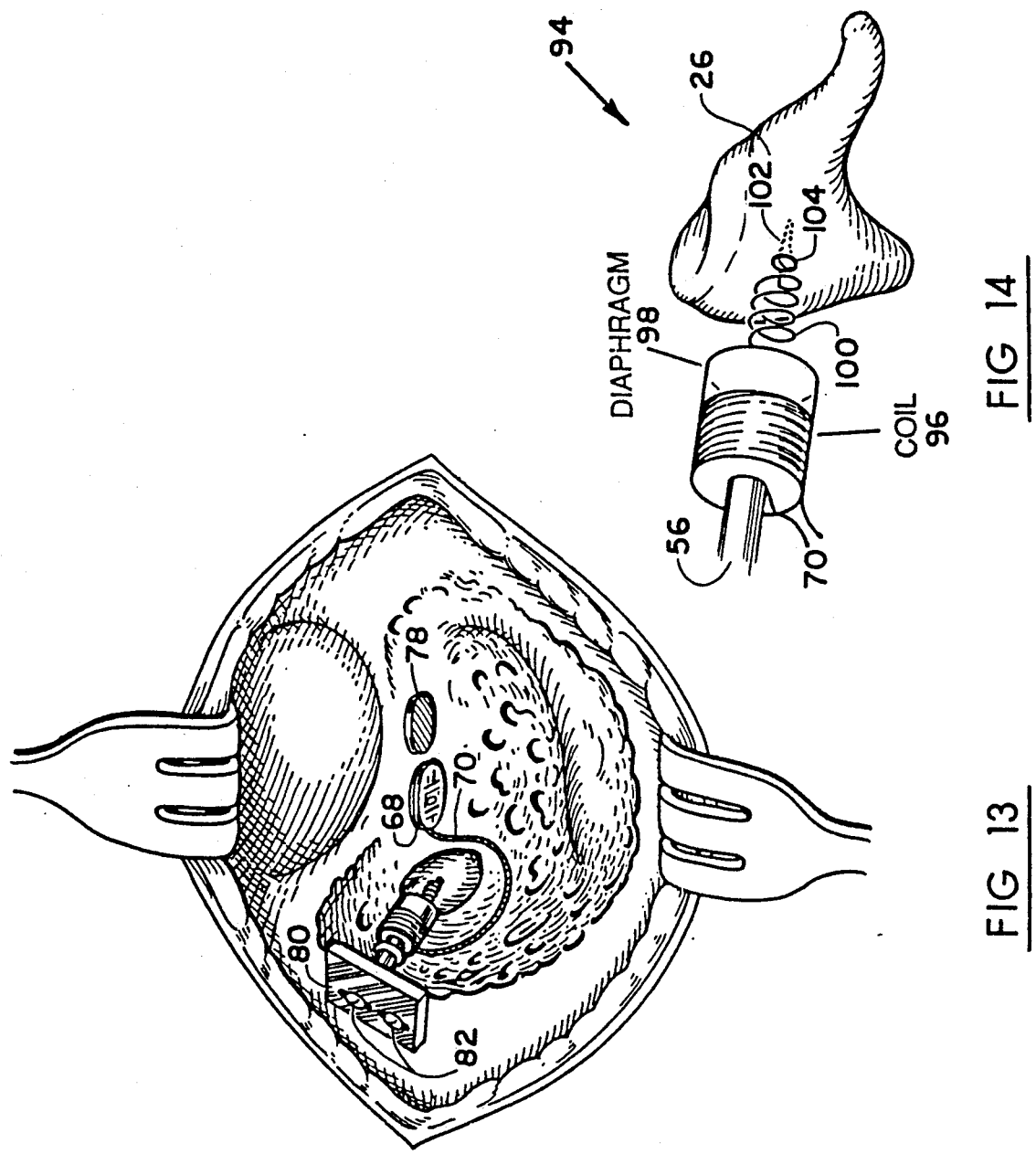

PARTIALLY IMPLANTABLE HEARING AID DEVICE

This is division of application Ser. No. 07/258,788 filed Oct. 17, 1988, now U.S. Pat. No. 4,957,47.

BACKGROUND OF THE INVENTION

1. Field of the Invention

The present invention relates, in general, to hearing devices and, in particular, to implantable hearing devices.

2. Description of the Related Art

With the advent of the operating microscope in the 1950's a newly born field of otology and microsurgery emerged. The development of tympanoplasty and stapedectomy have led to the amelioration of many varieties of conductive hearing loss. Even some sensorineural hearing losses have been successfully treated using microsurgical techniques.

Despite these surgical accomplishments, however, 20 million people in the United States of America still suffer from various degrees of hearing loss. While the vast majority of the people in this group are candidates for conventional hearing aid use, in reality only approximately 15 percent becomes users of an amplification device to overcome their hearing loss. Several factors, such as sound distortion, discomfort of fit, and cosmetic appearance are ostensibly to blame for this low incidence of conventional hearing aid use.

Volta, in 1800, first introduced the concept of stimulating the ear by using electricity. The carbon hearing aid first appeared about the turn of the century. Another landmark development was the vacuum tube hearing aid, introduced in the late 1930's, which, in time, was supplanted in the 1950's by the transistor-operated systems. All conventional hearing aids now use transistors and integrated circuits to improve frequency response, reduce size, lower harmonic distortion and increase flexibility of fit as compared to their predecessors, yet perhaps not to the ultimate satisfaction of each potential user.

The conventional hearing aid is composed of a microphone, an amplifier, a battery as a power source, and a speaker or earphone (commonly referred to as a receiver in the hearing aid industry). The implantable hearing device has the same basic components, except that the speaker is replaced by a driving vibrating component, such as an electromagnetic coil or a piezoelectric system of bimorph design. Environmental sound energy, as it passes through either device, is converted by the microphone into an electrical signal which is routed to an amplifier. In the conventional hearing aid, the speaker transduces the amplified electrical signals into acoustic energy, which is then transmitted to the tympanic membrane and ossicular chain. In the implantable hearing device, the speaker is eliminated, being replaced by the vibratory component which drives the ossicular chain.

Some investigators have directed their efforts to the needs of the hard-of-hearing patient, designing systems intended to circumvent many of the problems of the conventional hearing aid. Rutschmann, et al, in 1959, described auditory stimulation by the use of alternating magnetic fields acting on permanent magnets fixed to the ear drum. In 1967, investigators at the University of Pittsburgh, Department of Electrical Engineering, designed the first implantable hearing aid of this type. A U.S. Patent was granted but no further animal or human research has been reported.

U.S. Pat. No. 3,209,081 to Ducote, et al. discloses a hearing aid in which a sound amplifier and transmitter unit, carried on the body of the user, is used to transmit radio frequency signals to a remote receiver that is implanted subcutaneously against the skull of the user in a concealed position.

U.S. Pat. No. 3,346,704 to Mahoney discloses a hearing aid unit adapted to be implanted within the mastoid antrum of the user. The unit comprises a microphone, a battery, an amplifying system, and a speaker. A microphone tube extends from the microphone to a point beneath the skin and behind the ear of the user to transmit sound from the environment to the microphone, while a speaker tube extends from the speaker through the mastoid antrum into the middle ear space behind the ear drum to transmit the sound thereto.

Wingrove, U.S. Pat. No. 3,594,514, discloses an implantable hearing aid having a piezoelectric ceramic element mounted adjacent to the auditory conductive system of the middle ear to impart vibration thereto. Electrical circuitry connected to the piezoelectric element provides electrical signals representative of sound waves.

Goode's 1970 article on the state of the art in implantable hearing aids rekindled interest in this approach and progress continued throughout the early 1970's through the work of Glorig, et al., Vernon, et al., and Fredrickson, et al. who explored the feasibility of different implantable systems. Patent activity in that time frame includes U.S. Pat. No. 3,764,748 to Branch, et al; U.S. Pat. No. 3,870,832 to Fredrickson, and U.S. Pat. No. 3,882,285 to Nunley, et al.

Branch, et al., supra, discloses several hearing aid configurations for implantation within the middle ear cavity interiorly of the ear drum to the ossicle bone chain. Auditory signals picked off the ear drum are subsequently amplified and/or transmitted to natural and/or solid-state sound receiving mechanisms located on the oval window, the round window, or the promontory leading into the inner ear. The tensor tympani and stapedial muscles prevent loud sounds from damaging the inner ear.

Fredrickson, supra, employs an implanted coil and magnet in the ear after removal of the incus. The magnet is fastened to the head of the stapes and the coil, when energized by electrical signals from a sound transducer, produces a magnetic field which interacts with the magnetic field of the magnet. This interaction of the two magnetic fields causes movement of the stapes in the same manner as it is normally activated by the incus.

Nunley, et al., supra, discloses an implantable hearing aid which is implanted in a hollowed-out portion of the skull adjacent to the ear canal. A microphone part is connected to the ear canal which receives sound that enters the ear and transforms it into energies which are transmitted via mechanical means to the movable portions of the middle ear. In this fashion, a parallel sound path is provided which augments and supports the transmission of sound to improve hearing.

Advances in technology in the 1980's have spurred additional efforts. Suzuki, et al. and Yanagihara, et al. have published reports which describe middle ear implants in animals and humans using a piezoelectric vibrator of bimorph design. Several of their patients have reported good amplification and high fidelity of sound perception; indeed, the efforts of the Japanese group constitutes a major breakthrough in implantation devices.

Tjellstrom, et al., in 1981, 1983 and 1985, developed another variation of an implantable device. This system used a bone conduction "hearing aid" anchored directly to the temporal bone by implanted osseo-integrated titanium screws which exit to the surface percutaneously. While the incidence of infection has been low in the implanted subjects, the device has not been received altogether enthusiastically by many patients, ostensibly due to its design. It is helpful in patients with 45 dB or better bone condution. In 1985, Hough, et al. introduced a modification of the temporal bone stimulator for patients with bone conduction thresholds of 25 dB hearing loss or better. In this device, the titanium bone conduction vibrator is screwed into the temporal bone and no electronics are used except for a radio link coils to transmit the electrical signal transcutaneously. A vibrating coil activates the screw implanted in the bone. An ear-level and body-borne variant of this system have been presented to date. Although the body-borne system provides about 10 dB more gain than the ear level device, it has been less accepted by patients than the ear level device. See U.S. Pat. No. 4,606,329 to Hough for further details. Neither device (body-borne or ear level) has been quite as efficient as the Tjellstrom implant, perhaps because they employ indirect coupling through radio frequency transmission rather than direct bone conduction stimulation. Revisions of the electronic design may very well improve the efficiency of the bone conduction temporal bone stimulator of Hough, and since the device has U.S. Food and Drug Administration (FDA) approval, it should receive considerable clinical application in the United States and abroad. For a description of a particular type of coupling to a bone-anchored hearing aid, see U.S. Pat. No. 4,498,461 to Hakansson.

In 1987, Hough et al. reported on a middle ear implantable hearing device using electromagnetic principles applied to humans undergoing middle ear surgery under local anesthesia. Although the device was functional, its electrical power consumption was excessive.

Ko, Maniglia and Zhang also reported, in 1987, their experience with an electromagnetic middle ear hearing aid using direct stimulation of the stapes. Goode, et al. have experimented with a piezoelectric system to produce stapes vibration in fresh human temporal bones. Heide, et al. in 1988 presented the advantages of an electromagnetic hearing aid in the ear canal driving a magnet glued to the ear drum. Finally, Goode has recently reported encouraging results with another design in which another electromagnetic canal device similar in principle and design that stimulates a samarium cobalt magnet glued to the ear drum. However, the magnet glued to the ear drum only stays in place temporarily, and a better system is necessary.

Thus, while technological advances in the conventional hearing aid industry have succeeded in miniaturizing the components and improving the efficiency and gain of these devices, there are still problems to be solved. Some of the drawbacks associated with the conventional hearing aid are: high internal noise, acoustic feedback, limited fidelity due to sound distortion and a limited frequency response range. Additionally, many hearing aid styles are considered to be cosmetically unattractive, overly conspicuous, or even uncomfortable if they employ a tightly fitting earmold. As a consequence, a highly efficient, totally concealed conventional hearing aid is not yet available. Finally, the candidacy of a given person for hearing aid use may also be restricted on medical grounds because of such problems as chronic middle ear infections, stenosis or atresia of the external auditory canal, or prior radical mastoidectomy.

In theory, the attractiveness of an implantable hearing device lies in its ability to overcome many of the drawbacks mentioned above for the conventional hearing aid. However, if any implantable device is to provide a viable alternative to the conventional hearing aid, the device must not only overcome many of these drawbacks but it must also minimize all potential risk factors introduced by the surgical procedure. It should be made out of biocompatible materials and have the lowest risk possible regarding middle ear or inner ear complications. Ideally, its technical design should be trouble-free for many years so that the need for revision surgery is minimal. Finally, it should have the following advantages: (1) totally concealed cosmetically; (2) highly efficient power consumption; (3) high sound fidelity; (4) broad, flat frequency response; (5) minimal sound distortion; (6) elimination of ringing feedback; (7) adequate acoustic gain; and (8) be flexible and versatile so as to be applicable to cases involving conductive as well as sensorineural hearing loss, and to all age groups, especially the pediatric age group that would probably derive the greatest benefit from such a device, because of many more years of potential use.

SUMMARY OF THE INVENTION

The present invention provides a new and novel semi-implantable hearing device which overcomes the drawbacks of prior art devices, achieves the aforesaid advantages, and minimizes the risk factors introduced by the surgical procedure itself.

Accordingly, one aspect of the present invention is drawn to a totally concealed, partially implantable hearing device having a replaceable outer ear canal unit and an implanted magnet attached to the malleus bone of the ear. The replaceable ear canal unit receives acoustic energy or sound waves that enter the ear and travel down the outer ear canal to the unit. A microphone detects the sound waves and, with the help of a battery and an electronic amplifier, transforms the sound waves into amplified electrical signals. The electrical signals activate an electromagnetic driving coil, i.e., a coil of wire wrapped around a ferrite alloy core, which creates a magnetic field that varies in response to the sound waves detected by the microphone. The magnetic field created by the electromagnetic driving coil interacts with the magnetic field created by the magnet, creating a force which vibrates the magnet and the malleus bone to which it is attached. To insure that the magnet is securely attached to the malleus bone, a pair of titanium self tapping mini-screws are inserted through a hole in the magnet and inserted through a hole in the magnet and inserted into two man-made microcavities created in the malleus bone with the aid of a KTP 532 laser. Once the screws are inserted into the malleus bone, they are allowed to osseo-integrate for a three month period. After this period of time, the replaceable outer ear canal unit is put into use. The $SmCO_5$ magnet would weigh about 30 to 35 mg and the distance between this magnet and the external ear canal unit would be 3 to 5 mm.

Another variation of this system consists of placing the magnet encased in a titanium dish anchored to the lateral aspect of the incus. Two holes are made in the body of the incus, using the KTP 532 laser. The titanium extension of the dish is secured to the incus by two self tapping screws introduced through the previously made holes.

Another aspect of the present invention is drawn to a totally concealed, partially implantable hearing device having a replaceable outer ear canal unit having means for generating radio frequency waves responsive to acoustic energy or sound waves that enter the ear and travel down the outer ear canal to the unit. Again, a microphone detects the sound waves and, with the help of a battery and an electronic amplifier, transforms the sound waves into amplified electrical signals. In this aspect, however, the amplified electrical signals are sent to an external induction coil or radio signal transmitting antenna to be converted into amplitude modulation (AM) radio frequency waves that are transmitted to an internal induction coil implanted under the skin in the outer ear canal wall. An implanted electromagnetic driving coil, connected to the internal induction coil, again creates a magnetic field that varies in response to the sound waves detected by the microphone. This magnetic field interacts with another magnetic field created by a magnet attached to a bone in the ossicular chain in the ear. This interaction causes a force which vibrates the magnet and the bone to which it is attached. In one case, the bone to which the magnet is attached is the stapes; in another case the magnet is attached to the incus; while in a third case there is an electromagnetic-mechanical system having a very thin metal diaphragm attached to a titanium coil spring secured to the incus body, using a self-tapping titanium screw introduced through a hole, KTP 532 laser made. In another design the titanium spring coil is attached to a cup-bumper which "sits" on the stapes head.

Still another aspect of the present invention is drawn to a partially concealed, partially implantable hearing device having a replaceable hidden external unit adapted to be located externally and medially to an upper portion of a pinna of an ear, rather than being located inside the outer ear canal of the ear. A microphone detects the sound waves and, with the help of a battery, an electronic amplifier and an external induction coil, the sound waves are converted into amplitude modulation (AM) radio frequency type waves for transmission to an internal induction coil implanted under the skin behind the ear. An implanted electromagnetic driving coil, connected thereto, creates a magnetic field that varies in response to the sound waves detected by the microphone. The magnetic field created by a magnet attached to a bone in the ossicular chain in the ear interacts with the magnetic field created by the electromagnetic driving coil, causing the magnet and the bone to which it is attached to vibrate. Again, in one case, the bone is the stapes bone; in another case the bone is the incus; while in a third case the electromagnetic-mechanical system mentioned above is employed. In order to remote control the in ear canal unit another unit handheld, pocket type, similar to a remote control television system would be used featuring on and off and volume, up and down switches, activated by radio frequency transmission.

The various features of novelty which characterize the invention are pointed out with particularly in the claims annexed to and forming a part of this disclosure. For a better understanding of the present invention and the advantages attained by its use, reference is made to the accompanying drawings and descriptive matter in which preferred embodiments of the invention are illustrated.

BRIEF DESCRIPTION OF THE DRAWINGS

FIGS. 9 and 10 show a modified version of the embodiment of FIGS. 6, 9 and 10 illustrating an electromagnetic-mechanical driving coil which activates a very thin metal membrane attached to an intermediate spring coil connected to a cup-bumper which "sits" on the stapes head.

FIGS. 13 and 14 show a modified version of the embodiment of FIGS. 11 and 12. An electromagnetic-mechanical system in which an electromagnetic coil activates a diaphragm made out of a very thin (10 microns) metal membrane attached to the body of the incus by means of a titanium intermediate spring coil. A self tapping titanium screw secures the eyelet of the coil on the incus, through a laser made hole.

DESCRIPTION OF THE PREFERRED EMBODIMENTS

Figure 1:
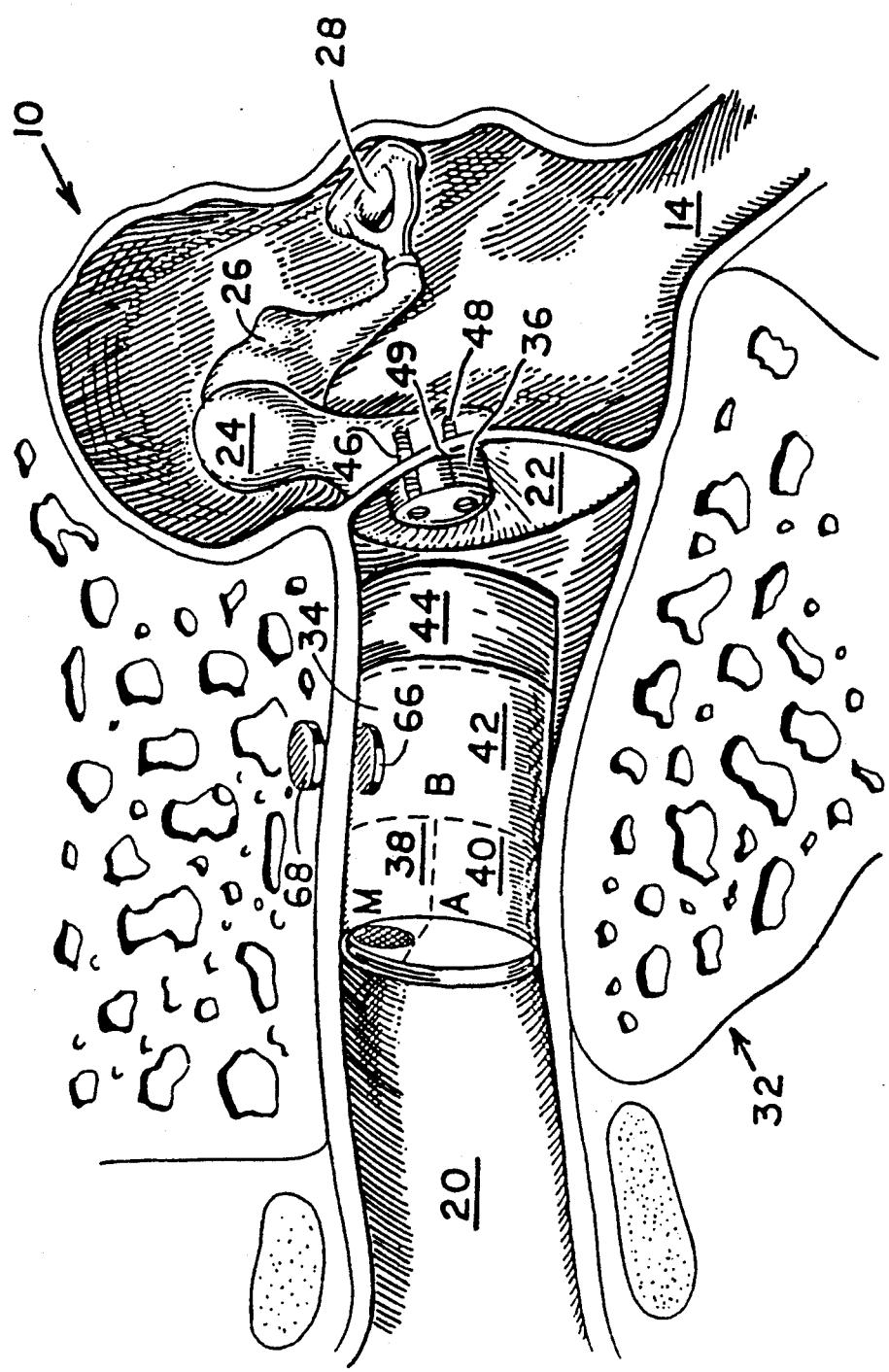
FIG. 1 shows a coronal cut view of an ear which has received a first embodiment of the invention in which the magnet has been secured to the malleus bone in the ossicular chain.
Figure 2:
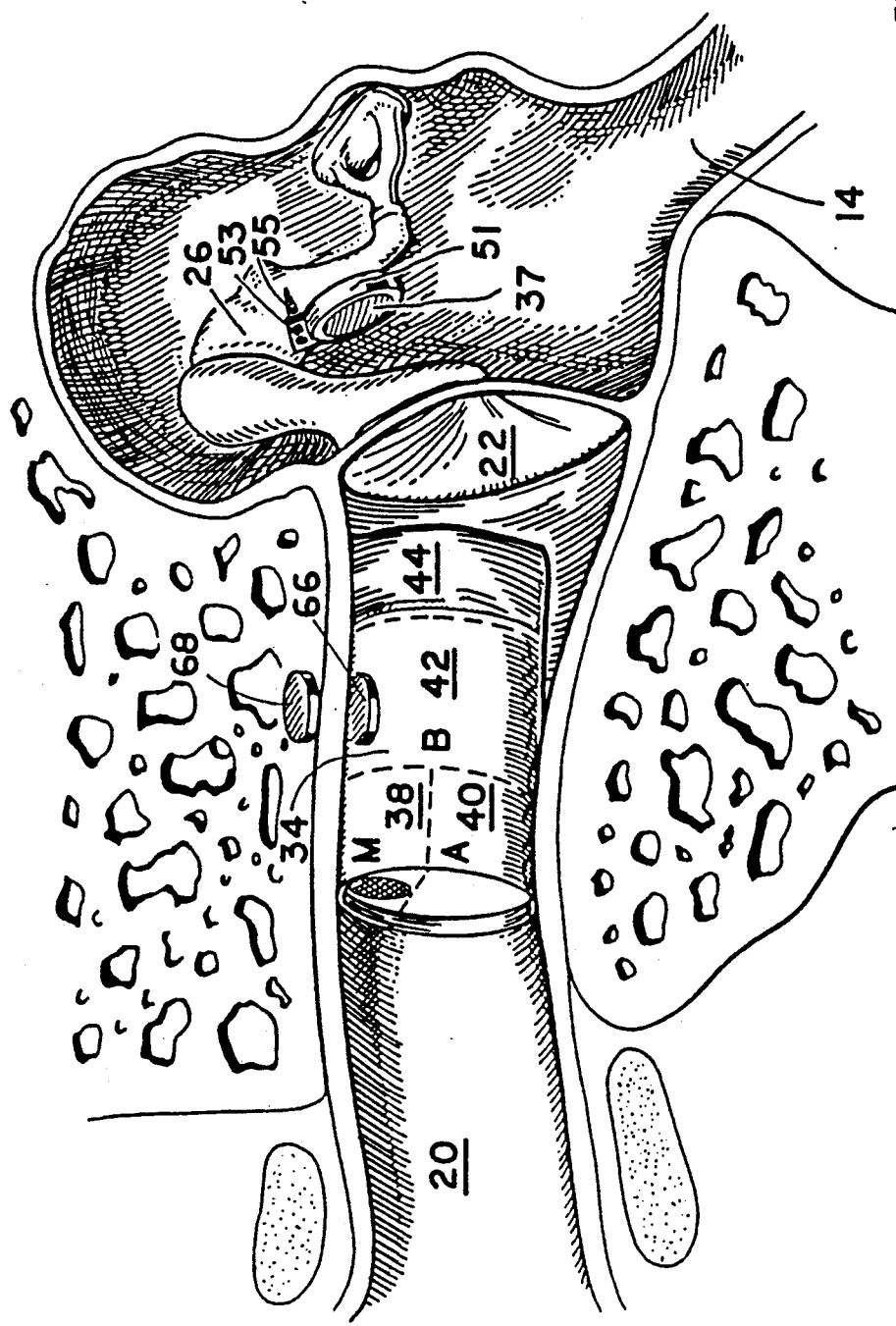
FIG. 2 shows a coronal cut view in which the magnet is secured to the body of the incus in a titanium dish.

Referring to the drawings generally, wherein like numerals designate the same element throughout the several drawings, and to FIGS. 1 and 2 in particular, there are shown cross-sectional views of an ear, generally referred to as 10, which has received the hearing device of the present invention.

Figure 5:
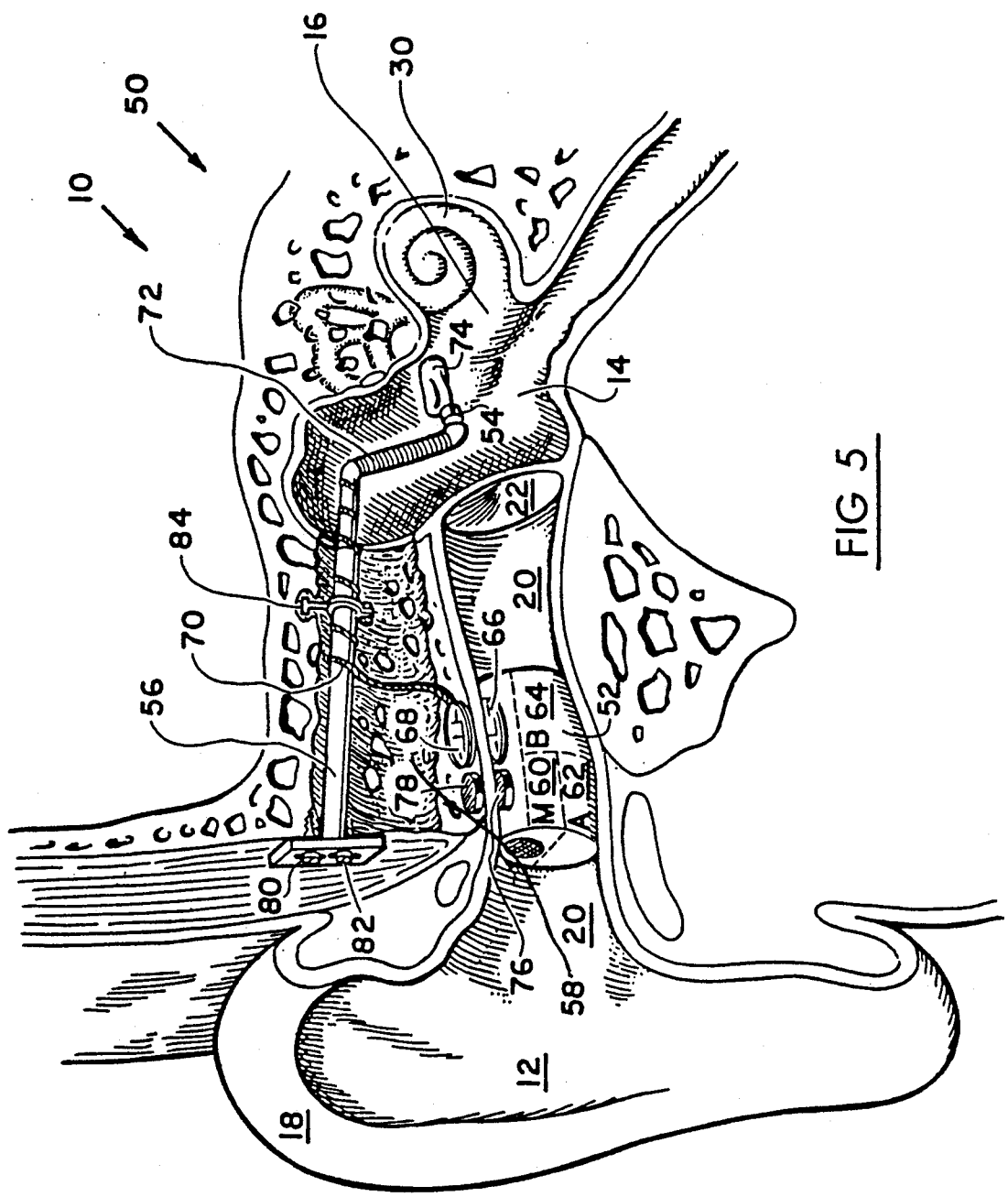
FIG. 5 shows a coronal cut view of an ear which has received a second embodiment of the invention in which the magnet has been secured to the stapes bone in the ossicular chain, induction coils send/receive the radio frequency waves through the skin of the outer ear canal wall, and where the electromagnetic driving coil is attached to a supporting shaft inserted in the mastoid-attic cavity.

The ear 10 is made up of an outer ear 12, a middle ear 14, and an inner ear 16 (as best shown in FIG. 5). The outer ear 12 includes an auricle or pinna 18, and an outer ear canal 20. The pinna 18 collects acoustic energy or sound waves from the environment and directs them into the outer ear canal 20 which conveys the sound waves by air conduction to a tympanic membrane or ear drum 22, which separates the outer ear 12 from the middle ear 14.

The middle ear 14 contains a series of three tiny interconnected bones: the malleus (hammer) 24; the incus (anvil) 26; and the stapes (stirrup) 28. Collectively, these three bones are known as the ossicles or the ossicular chain. The malleus 24 is attached to the tympanic membrane 22 while the stapes 28, the last bone in the ossicular chain, is attached to the oval window (inner ear) (not shown).

Sound waves that travel down the outer ear canal 20, strike the tympanic membrane 22 and cause it to vibrate. The malleus 24, being connected to the tympanic membrane 22, is thus also set into motion, along with the incus 26 and the stapes 28. These three bones in the ossicular chain act as a set of levers to amplify the tiny vibrations received by the tympanic membrane 22. By the time the vibrations are transmitted to the oval window (not shown) the pressure vibrations received by the tympanic membrane 22 have been magnified by as much as 22 times. The stapes vibrates in turn, causing fluid in a spiral structure known as the cochlea 30 to move along its length. Very small hairlike cells (not shown) in the cochlea 30 are stimulated by the movement of fluid in the cochlea 30. There, hydraulic pressure displaces the inner ear fluid and mechanical energy in the hair cells is transformed into electrical impulses which are transmitted to neural pathways and the hearing center of the brain (temporal lobe), resulting in the perception of sound.

Referring now to FIG. 1, there is shown a first embodiment of the present invention, drawn to a totally concealed, partially implantable hearing device generally referred to as 32. The hearing aid 32 includes a replaceable outer ear canal unit 34 and a magnet 36. The outer ear canal unit 34 would be inserted into the outer ear canal 20 by means of a forceps (not shown) similar to the type used in bronchoscopy for foreign body removal. The unit 34 is encased and hermetically sealed in a silicone mold for protection against corrosion from body fluids and for ease of insertion into the outer ear canal 20. The size of the unit 34 is generally adapted using an ear canal impression mold (not shown) to be closely received by the outer ear canal 20 without discomfort to the wearer and may advantageously be cylindrical or oval in shape. It must conform to the shape of the outer ear canal 20. For individuals with narrow outer ear canals 20, canalplasties could be performed to allow accommodation of the unit 34.

The unit 34 receives acoustic energy or sound waves which are collected by the pinna 18 and conveyed down the outer ear canal 20. The unit 34 includes a microphone or transducer 38 for converting the acoustic energy or sound waves into electrical signals representative thereof; an amplifier for 40 for amplifying these electrical signals, a power supply or battery 42 for providing electrical energy to the microphone 38 and amplifier 40; and an electromagnetic driving coil 44 for generating a first magnetic field responsive to the amplified electrical signals representative of the sound waves received by the unit 34.

Advantageously, the microphone 38 can be an electret microphone, such as manufactured by Knowlls Corporation. Typically, the microphone 38 would be placed on the end of the unit 34 facing the ear or pinna 18 associated with the outer ear canal 20 which received the unit 34. The amplifier 40 may advantageously be a microchip unit. The battery 42 may advantageously be of the nickel-cadmium or manganese/dioxide lithium cell type, chosen for their long life to minimize insertion and replacement of the unit 34 into the outer ear canal 20. Since the unit 34 is easily insertable and replaceable by means of the forceps (not shown) mentioned earlier, repairs of the unit 34 or changing of the battery 42, when necessary, can easily be achieved. If desired, a spare unit 34 could be provided to a patient to be worn in the interim should repairs to the unit 34 be necessary, to eliminate "down time".

The electromagnetic driving coil 44 would typically have a ferrite-alloy core of dimensions of 9 mm × 2 mm wrapped with approximately 3,000 turns of AWG (American Wire Gauge) #55 copper wire, resulting in a highly efficient coil. AWG #55 copper wire has a nominal outside diameter of less than 1.8 mils (1 mil = 0.001 inch = 0.025 mm). Generally, the electromagnetic driving coil 44 would be placed on an end of the unit 34 opposite the end having the microphone 38.

The magnet 36 is securely attached to the malleus bone 24 in the ossicular chain of the ear 10, thus eliminating the speaker/earphone/receiver (not shown) of conventional hearing aids. While others (Goode, Bojrab, et al) tried this system in human volunteers with favorable results, difficulties have been encountered in adequately securing the magnet onto the tympanic membrane 22. Different adhesives have been used with poor results: the magnet becomes dislodged from the tympanic membrane 22 and the system malfunctions. In contrast, the present invention circumvents this problem by securing the magnet 36 to the handle of the malleus 24 by means of two mini cavities 46 therein. A KTP 532 laser (not shown) would be used to create the two mini cavities 46, which would then be the receptacle for two titanium, self tapping screws 48. A titanium abutment 49 is inserted through holes drilled in the magnet disc advantageously, a rare earth, samarium cobalt $SmCO_5$ magnet and screwed with threads situated in the head of the titanium screws 48 which has been previously inserted in the malleus 24. A lapse of 3 months from the time of insertion of the screws 48 to the placement of the abutment 49 is necessary for biointegration. Biointegration takes place under sterile conditions created as follows. A small flap of ear drum on the malleus handle is reflected exposing bare bone. The minicavities 46 are created with the laser and the self-tapping screws 48 are applied. The flap of ear drum covers the head of the screws 48. Healing takes place, and after 3 months the head of the screws 48 are exteriorized and the titanium abutment 49 with the samarium cobalt magnet 36 is secured to the head of the screws 48. Then the outer ear canal unit 34 would be inserted in the outer canal 20.

The location of the end of the electromagnetic driving coil 44 with respect to the end of the magnet 36 is critical for optimum efficiency, since the degree of interaction between the first magnetic field created by the electromagnetic driving coil 44 and the magnet 36 is inversely proportional to the cube of the distance there between. For example, if the distance between these two elements 36 and 44 is doubled from about 5 mm to 10 mm, the force from the electromagnetic driving coil 44 acting on the magnet 36 is reduced eightfold. Preferably, the distance between the magnet 36 and the electromagnetic driving coil 44 should be approximately 3 to 5 mm. In practice, a patient using the hearing aid 34 would be trained to insert the unit 34 with the forceps (not shown) into the outer ear canal 20 and, when noticing optimum hearing improvement, would remove the forceps (not shown) without disturbing the position of the unit 34. Removal of the unit 34, for repairs or replacement of the battery 42 would be accomplished by the reverse procedure.

Figure 3:
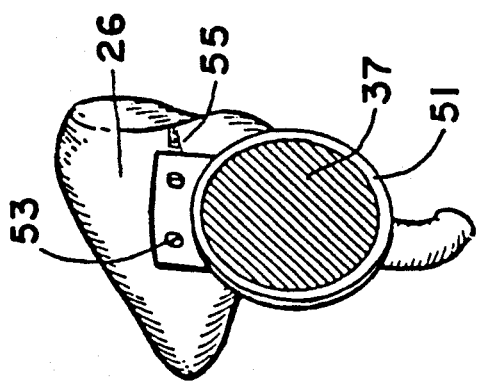
FIGS. 3 and 4 show detail of the titanium disc-magnet as shown in FIG. 2 and how it is anchored to the body of the incus.
Figure 4:
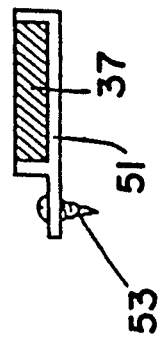

Referring to FIGS. 2, 3, and 4, it shows another version of FIG. 1 whereby the magnet 36 in a variant form 37 is secured to the body of the incus in a titanium dish 51. The distance between ear drum and unit 34 would be to 3 mm. Magnets 66 and 68 ($SmCO_5$) secure unit 34 in each ear canal 20. The incus 26 would vibrate through the interaction of magnetic fields of coil 44 and magnet ($SmCO_5$) 37 in a titanium dish 51 secured to the incus body with self tapping titanium screws (53) introduced in laser (not shown) created cavities 55.

Referring to FIG. 5, there is shown a second embodiment of the present invention, drawn to a totally concealed, partially implantable hearing device generally referred to as 50. The hearing device 50 includes a replaceable outer ear canal unit 52, a magnet 54 securely attached to a location on a bone in the ossicular chain of the ear 10, and supporting shaft 56. The supporting shaft 56 is shown in FIG. 5 as being located in a mastoid-attic cavity 58; other locations are possible as will be discussed later.

The outer ear canal unit 52 receives acoustic energy or sound waves collected by the pinna 18 and conveyed down the outer ear canal 20, much in the fashion of the previously discussed outer ear canal unit 34. Similarly, the unit 52 includes a microphone or transducer 60, an amplifier 62, and a power supply battery 64 whose relative positions, structure and functions are substantially identical to those of their conterparts 38, 40 and 42, respectively, in the unit 34. The unit 52 would also be encased and hermetically sealed in a silicone mold for ease of insertion and removal and for protection against corrosion from body fluids. However, in contrast to the unit 34, the outer ear canal unit 52 also contains an external induction coil or radio frequency wave signal transmitting antenna 66. The microphone 60, the amplifier 62 and the battery 64 receive, amplify and convert the sound waves received by the unit 52 into electrical signals representative thereof. These electrical signals are then sent to the external induction coil 66 which generates amplitude modulation (AM) radio frequency waves reponsive to the acoustic energy or sound waves received by the unit 52.

Implanted under the skin of the wall of the outer ear canal 20 is an internal induction coil or radio frequency wave signal receiving antenna 68. Implantation of the internal induction coil 68 would typically be performed through a mastoidectomy approach, being laterally lodged in the posterior bony wall of the outer ear canal 20. The external induction coil 66 transcutaneously transmits the radio frequency waves, advantageously amplitude modulation (AM) radio frequency waves, representative of the sound waves received by the unit 52, to the internal induction coil 68. Wires 70 would interconnect the internal induction coil 68 to an electromagnetic driving coil 72 located adjacent to but spaced away from the magnet 54, which again is preferably a rare earth, samarium cobalt magnet. The electromagnetic driving coil 72 is supported by the supporting shaft 56. The electromagnetic driving coil 72 thus creates a first magnetic field, responsive to the sound waves or acoustic energy received by the unit 52, that interacts with the magnetic field created by the magnet 54, causing it and the bone in the ossicular chain to which it is attached to vibrate. As shown in FIG. 5, the bone in the ossicular chain could be a stapes bone 74; other bones in the ossicular chain are equally likely candidates.

The outer ear canal unit 52 would be inserted or removed from the outer ear canal 20 in a similar manner as described for the unit 34. However, to ensure that the unit's 52 external induction coil 66 is in approximate alignment with its counterpart internal induction coil 68, an external positioning magnet 76 is placed in the outer ear canal unit 52 near the outer surface thereof, while an internal positioning magnet 78 is implanted under the skin in the outer ear canal wall 20. The external and internal positioning magnets 76, 78, preferably also of the rare earth, samarium cobalt type, have magnetic fields that interact with each other, resulting in a holding force that holds the unit 52 at a selected position in the outer ear canal wall 20. Magnets 76 and 78 could also be used, in the first embodiment, to secure the outer ear canal unit 34 in the outer ear canal wall 20, if desired. The position of the external induction coil 66 and the external positioning magnet 76 on the unit 52 are chosen so that they are substantially adjacent their counterparts 68 and 78, respectively, implanted under the skin of the outer ear canal wall 20. Similarly, the microphone 60 is also arranged with respect to the external positioning magnet 76 and external induction coil 66 so that it faces the pinna 18 associated with the outer ear canal 20 which receives the unit 52 when the positioning magnets 76, 78 and the induction coils 66, 68 are substantially adjacent each other.

The electromagnet driving coil 72 must be placed at a precise distance away from the adjacent magnet 54. Preferably, this distance is approximately 2 mm. In this embodiment, the electromagnet driving coil 72 would typically have a ferrite-alloy core of dimensions 7 mm $\times$ 2 mm, wrapped with approximately 3,000 turns of AWG #55 copper wire.

The supporting shaft 56 is used to secure and position the electromagnetic driving coil 72 with respect to the magnet 54. In a preferred embodiment, the supporting shaft 56, is an L-shaped, titanium plate shaft capable of telescoping to increase or decrease its length so as to permit selection of the optimal coupling distance between the electromagnetic driving coil 72 and the magnet 54 (not shown). The end of the structure 56 opposite the end holding the coil 72 would be secured to the temporal bone structure by means of a plate 80 and screws 82, also preferably made of titanium. A hanger 84 having a set screw 86 provides an additional support and allows for fixation of the length of the telescoping intermediate structure 56.

Figure 6:
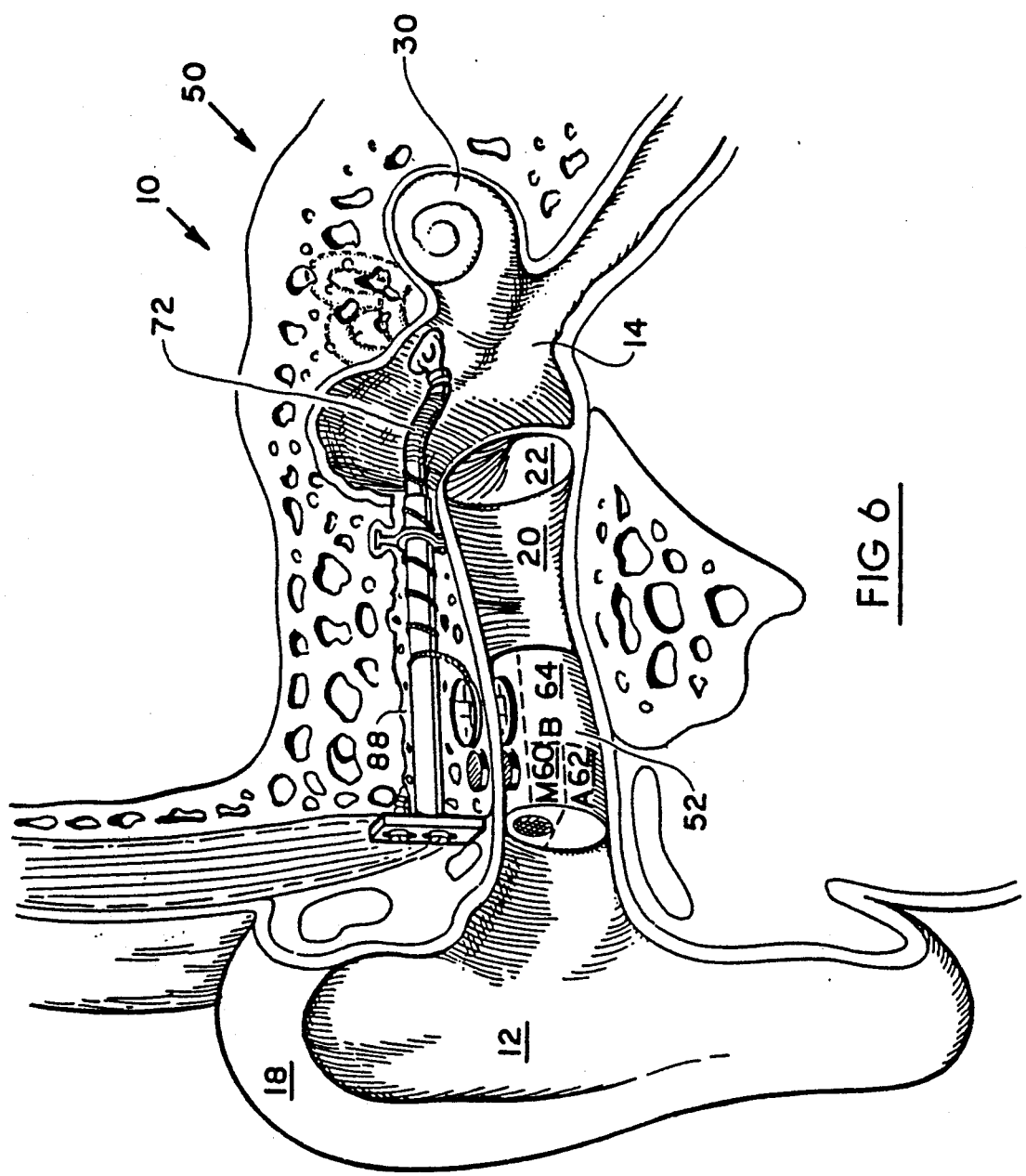
FIG. 6 shows a modified version of the third embodiment of FIG. 5 in which the intermediate structure is located in the posterior bony canal, closer to the outer ear canal wall of the ear.

FIG. 6 shows a modified version of FIG. 5 in which the supporting shaft 56 is located in the posterior bony canal 88 closer to the outer ear canal wall 20 of the ear 10.

Figure 7:
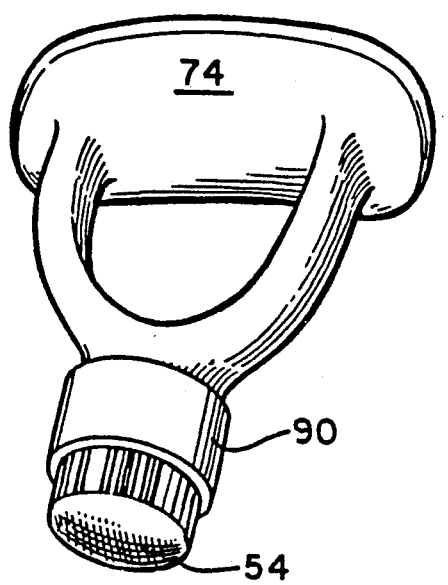
FIGS. 7 and 8 show the magnet implanted onto the head of the stapes bone by means of an intermediate plastipore cup.
Figure 8:
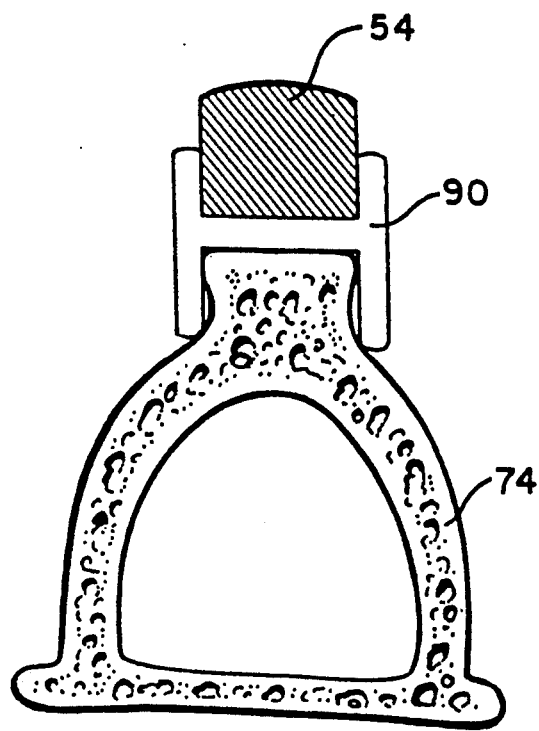

Referring to FIGS. 7 and 8, there is shown two close-up views of the stapes bone 74 to which the magnet 54 has been attached. An intermediate, biocompatible, plastipore cup 90 would preferably be used to glue the magnet 54 to the head of the stapes bone 74, rather than gluing the magnet 54 directly to the stapes 74. This arrangement facilitates, should the need arise, removal of the magnet 54 off of the head of the stapes 74 by means of simply cutting off the plastipore cup 90.

FIGS. 9 and 10 depict a modified version of FIGS. 5 and 6 whereby an electromagnetic-mechanical system 94 is selected. A ferrite-alloy is wrapped with 1300 turns of #45 copper wire 96. When energized, it activates the thin metal membrane 98 attached to a titanium spring coil 100 welded to a cup-bumper 102 which "sits" on the stapes head. The appropriate stiffness of the spring is critical to good function.

Figures 11, 12:
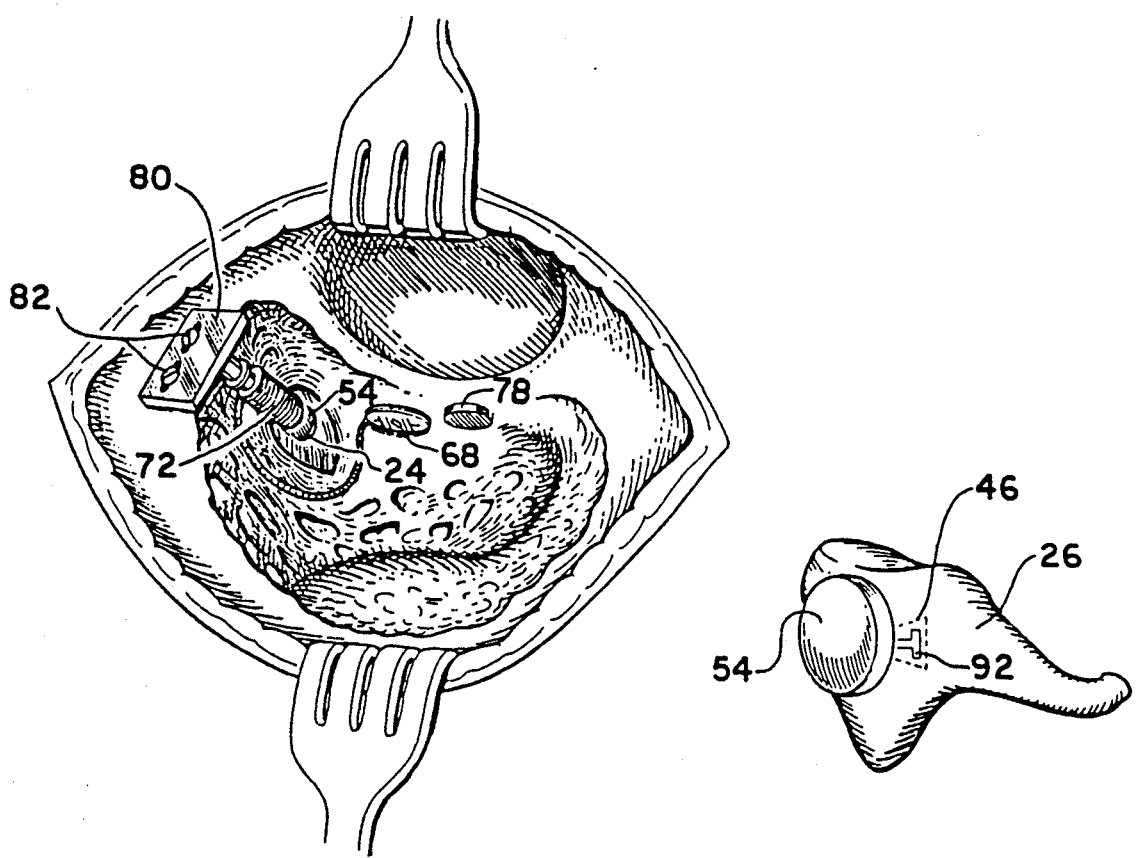
FIGS. 11 and 12 show another version showing the mastoidectomy-atticotomy surgical view presented when the intermediate structure and electromagnetic driving coil are positioned in the attic, and a close-up view of the implanted magnet when secured to the body of the incus in the ossicular chain which is intact. A hole is made with the laser and the magnet "T" extension is cemented into the incus.

Referring now to FIGS. 11 and 12, there is shown another modified version of FIGS. 5 and 6 showing, respectively, the surgical view presented when the intermediate structure and its attached electromagnetic driving coil 72 are positioned in the attic, and a closeup view of the implanted magnet 54 secured to the body of the incus bone 26. In general, it is advantageous to attach the magnet 54 directly to the head of the stapes 74 (via the intermediate plastipore cup 90) since less driving force is required to vibrate the stapes 74, resulting in reduced power consumption of the unit 52. However, in sensorineural hearing loss, in order to avoid an iatrogenic conductive hearing loss, it is desirable not to disconnect the ossicular chain. In such cases, the alternative approach shown in FIGS. 11 and 12 would be desirable. The magnet 54 is attached to the body of the incus bone 26, by means of a T-shaped pin 92 inserted and cemented with methyl methacrylate into a minicavity 46 placed into the incus bone 26. A laser (not shown) could again be used to create the minicavity 46 as described before. The titanium screw technique described earlier could also be applied to secure the magnet 54.

Referring now to FIGS. 13 and 14, there is shown an electromagnetic-mechanical system generally referred to as 94, in which an electromagnetic coil 96 activates a diaphragm 98 made out of a very thin (10 microns) metal membrane. Attached to the diaphragm 98 is a first end of a titanium spring coil 100; the attachement can be by soldering or other suitable means. The stiffness of the spring coil is critical in order to avoid a shock absorber effect. A hole 102 is again created by means of a laser (not shown) which would receive a self-tapping titanium screw 104, advantageously 3 mm long by 0.75 mm in diameter. A second end of the spring coil 100 is secured to the screw 104, thus coupling the diaphragm 98 to the body of the incus 26. Equally suited for the second or third (infra) embodiments of the invention, the electromagnetic-mechanical system 94 would be attached to the supporting shaft 56, and would vibrate the incus 26 by means of the diaphragm 98 and spring coil 100 in response to electrical signals, transmitted along wires 70, representative of received acoustic energy or sound waves detected by a microphone of the present invention.

Figure 15:
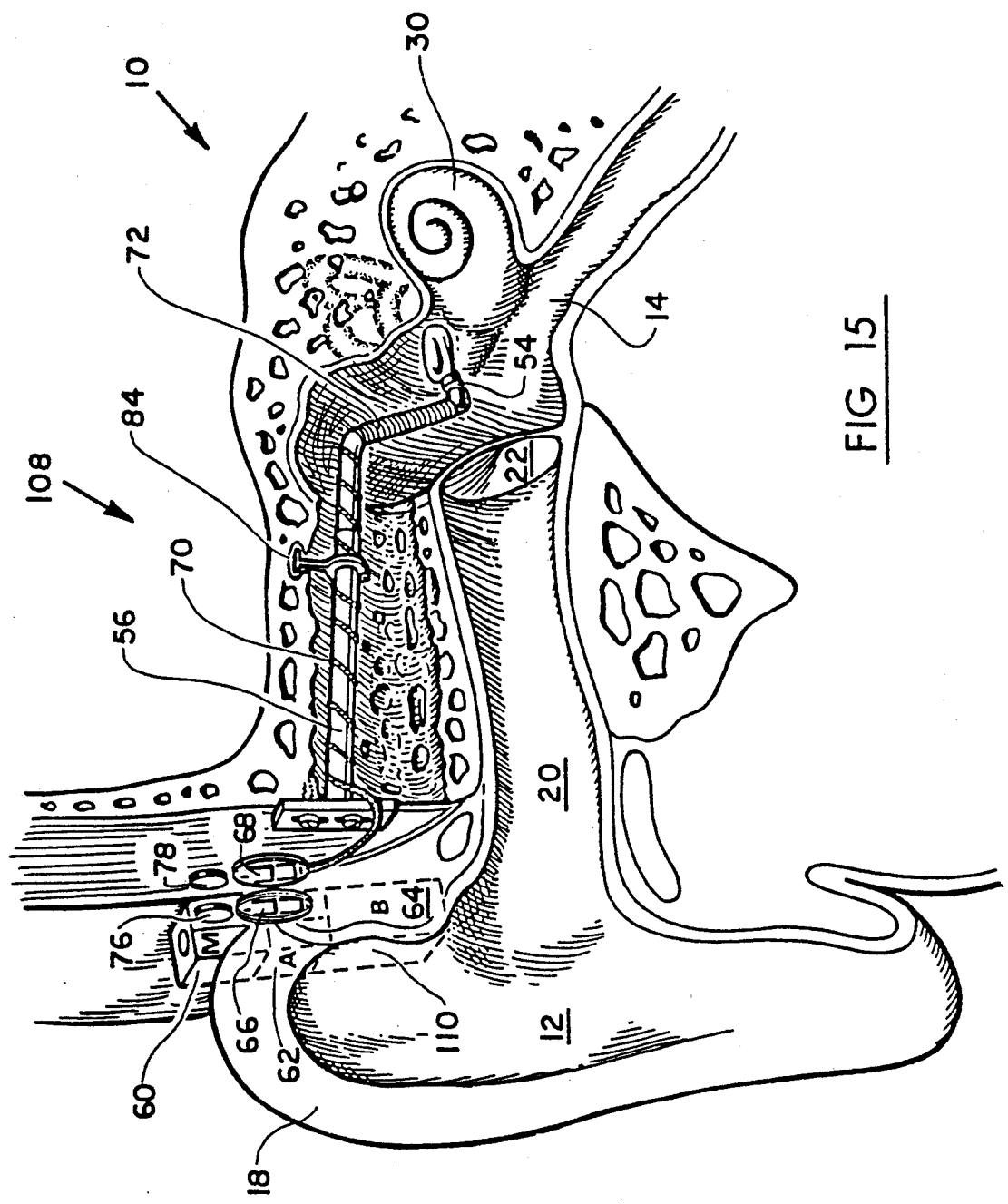
FIG. 15 depicts a behind the ear external unit which is secured in position by two strong $SmCO_5$ magnets. By radio frequency the two induction coils transmit electric impulses. This unit is a substitute of the in the ear canal unit to be used by patients with less manual dexterity. This behind the ear unit may activate any of the driving coils previously described, connected to the ossicular chain by the different embodiments. A modified version of this unit would be by means of direct coupling with a percutaneous osseo-integrated titanium screw. Direct wiring from the amplifier to the electromagnetic coil in the middle ear would then be used therefore eliminating the need for transcutaneous radio transmission. The titanium screw abutment would be directly connected to the behind the ear unit. No need for the $SmCO_5$ magnets to hold the unit would be required.

Referring now to FIG. 15, there is shown a third embodiment of the present invention, drawn to a partially concealed, partially implanted hearing aid generally referred to as 108. The hearing aid 108 includes a replaceable, partially hidden external unit 108, the magnet 60 securely attached to a bone in the ossicular chain, and the supporting shaft 56.

The external unit 110 is adapted to be located externally and medially to an upper portion of the pinna 18. The external unit 110 includes the microphone or transducer 60, the amplifier 62 and the power supply or battery 64, whose relative positions, structure, and functions are substantially identical to those shown and discussed in the second aforesaid embodiment. Since the external unit 110 is not inserted into the outer ear canal wall 20, it need not be encased and hermetically sealed in the silicone mold required for the previous embodiments.

To hold the external unit 110 at the selected external position located medially near the upper portion of the pinna 18 of the ear 10, external and internal positioning magnets 76, 78, respectively, are again provided. In this application, however, the internal positioning magnet 78 is implanted under the retroauricular skin behind the pinna 18 of the ear 10. The internal positioning magnet 78 interacts with and holds the external positioning magnet 76 and its attached external unit 110 at the selected position. If necessary, a transparent hook (not shown) attached to external unit 110 and hanging over the pinna 18 could be used to further stabilize the external unit 110 behind the pinna 18.

In operation, the microphone 60 of the external unit 110 receives acoustic energy or sound waves from the environment. The microphone 60, the amplifier 62 and the battery 64 receive, amplify and convert the sound waves received by the external unit 110 into electrical signals representative thereof as described earlier. These electrical signals are then sent to the external induction coil 66 which generates radio frequency waves responsive to the acoustic energy or sound waves received by the microphone 60 of the external unit 110 as described earlier.

The internal induction coil 68 is implanted under the retroauricular skin behind the pinna 18 of the ear 10 for transcutaneously receiving the radio frequency waves, advantageously amplitude modulation (AM) radio frequency waves, broadcast by the external induction coil 66. The positions of the external and internal induction coils 66, 68, external and internal positioning magnets 76, 78 and the microphone 60 is near the upper portion of the pinna 18 of the ear when the external unit is in place. This placement of the microphone 60 gives the best exposure to allow optimum sound reception from the environment.

Wires 70 interconnect the internal induction coil 68 to the electromagnetic driving coil 72 supported by the intermediate structure. The electromagnetic driving coil 72 creates a first magnetic field, responsive to the sound waves or acoustic energy received by the external unit 110, that interacts with the magnetic field of the magnet 54, causing it and the bone in the ossicular chain to which it is attached to vibrate. These vibrations are transmitted to the cochlea 30, leading to the eventual perception of sound in the hearing center of the brain.

The electromagnetic driving coil 72 would be substantially identical to that used in the aforementioned second embodiment, having a ferrite-alloy core of specified dimensions wrapped with approximately 2000 turns of AWG #45 copper wire. The intermediate structure again functions to position and secure the electromagnetic driving coil 72 at the preferred 2 mm distance from the magnet 54. Telescoping and fixation features of the intermediate structure allow for precise location of the electromagnetic driving coil 72, as well as for differences in anatomy and firm fixation.

The material for the magnet 54 and the positioning magnets 76, 78 may preferably be a rare earth, samarium cobalt material as before. The plastipore cup 90 would preferably again be used if the magnet 54 is to be attached to the head of the stapes bone 74; of course, attachment instead to the incus bone 26 may also be accomplished as previously described to address cases of sensorineural hearing loss, as well as the electromagnetic-mechanical system coupled with the stapes head.

Figure 16:
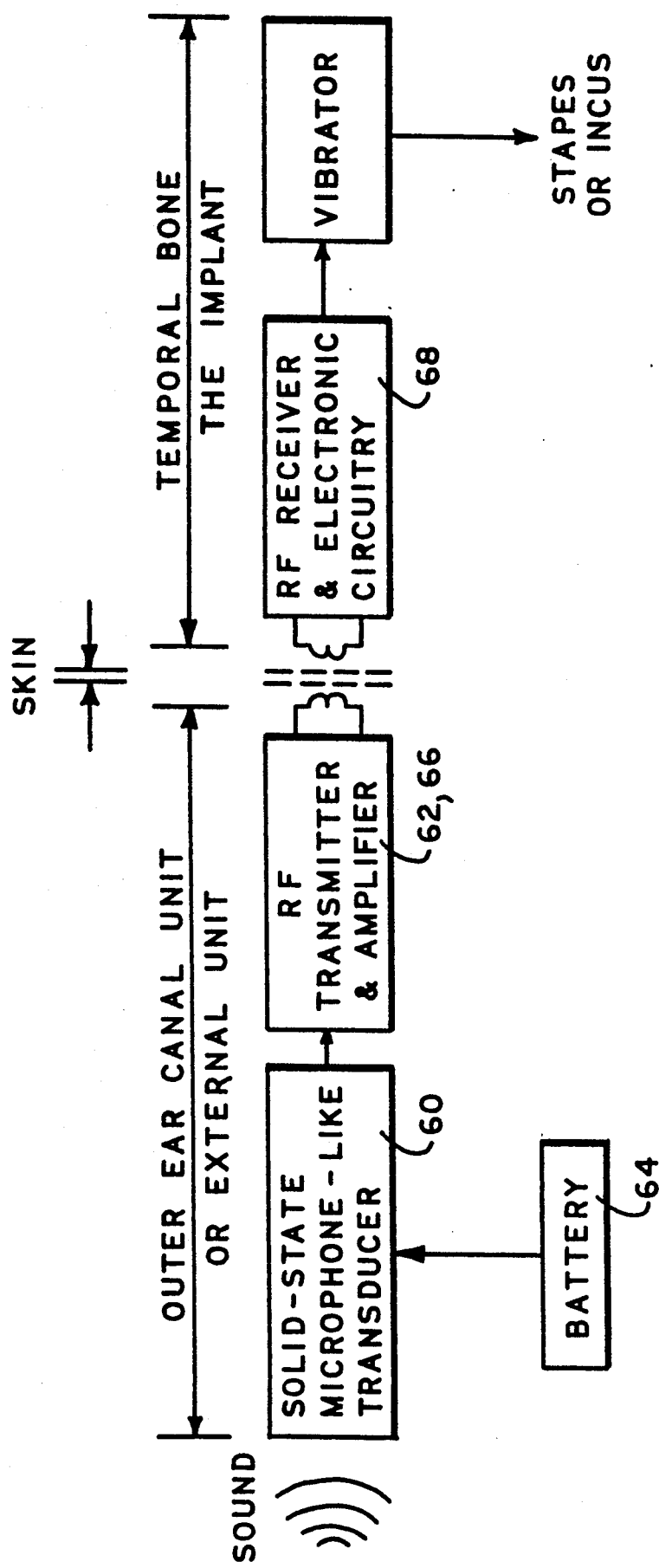
FIG. 16 shows a schematic electrical diagram of the partially implantable hearing aid of the present invention utilizing the external and internal inductions coils.

FIG. 16 shows a schematic electrical diagram of the partially implantable hearing aid of the present invention, applicable to the totally concealed, partially implanted embodiment 50 and the partially concealed, partially implanted embodiment 108. In the first embodiment, the RF transmitters and receivers would, of course, be omitted.

Figure 17:
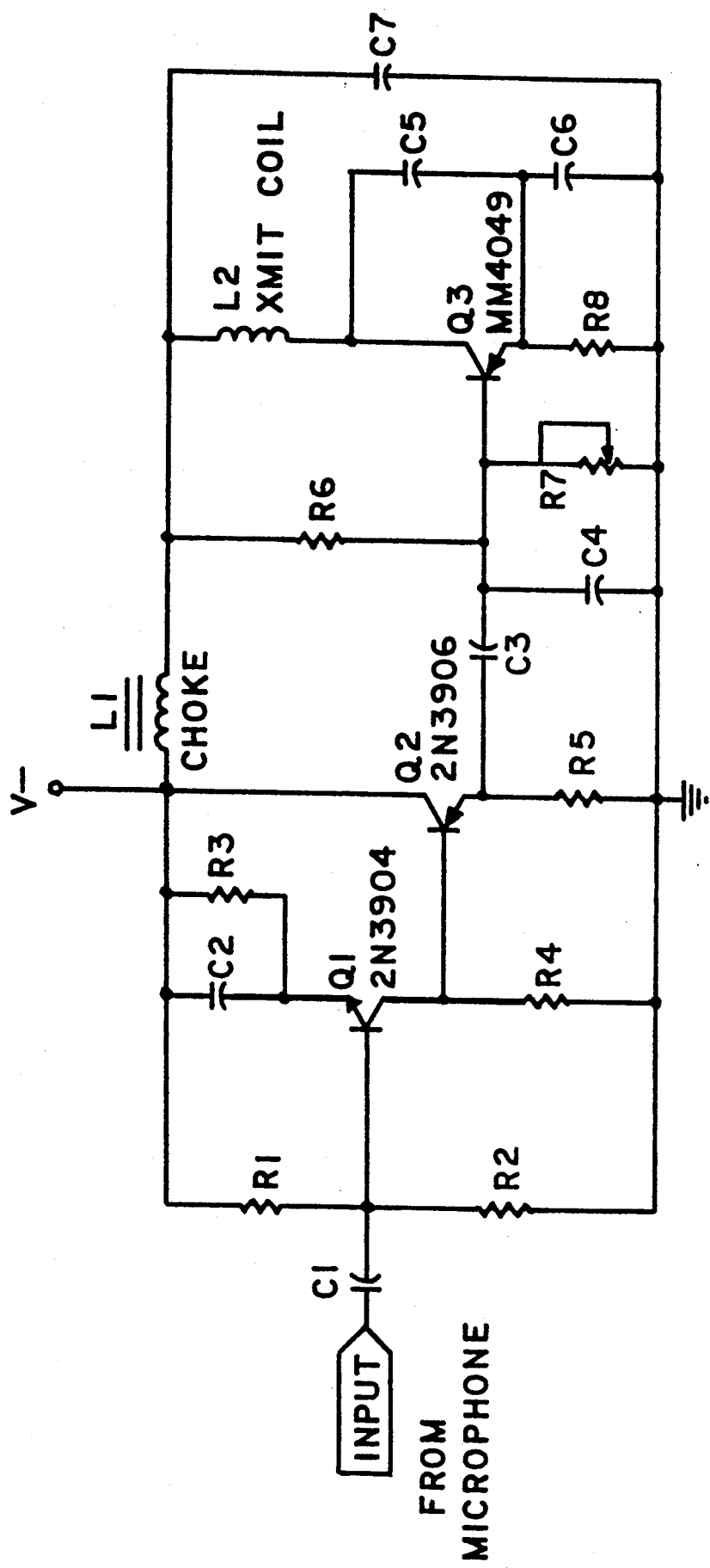
FIG. 17 shows a detailed electrical diagram of the amplifier and oscillator-modulator of the present invention (5 mega Hz).

FIG. 17 shows a detailed electrical diagram of the amplifier 40, 62 and oscillator-modular of the present invention. As indicated therein, the input to the circuit would come from the microphone 38, 60 and would convert the received acoustic energy or sound waves into electrical signals representative thereof.

Figure 18:
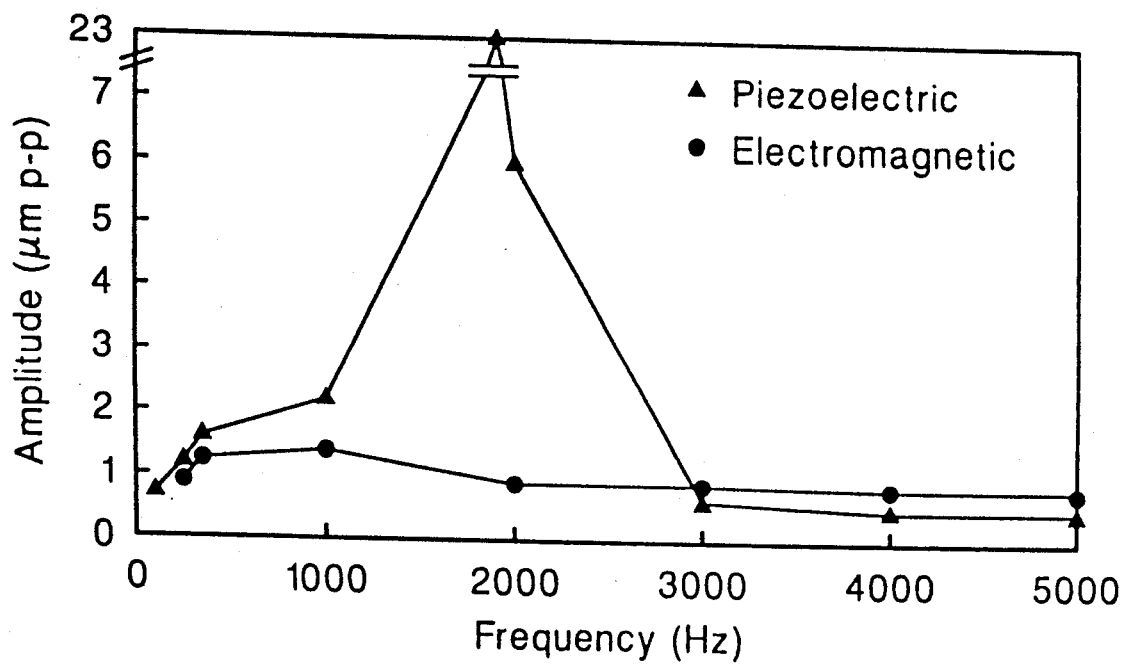
FIG. 18 shows a comparison of frequency response for a piezoelectric versus electromagnetic system as measured by a laboratory model.

The selection of an electromagnetic driving coil 72 for the present invention was a calculated decision based upon laboratory experiments designed to specify the microvibrational characteristics of the magnet-weighed ossicles of fresh cat and human temporal bones. The goal in this experiment was to determine the optimal type of vibratory stimulator for implantation. Specifically, it was necessary to deterine whether an electromagnetic or a piezoelectric circuit would produce a significantly different frequency response of stapedial vibration. The piezoelectric device tested in our laboratory showed a peak frequency response of 1.9 KHz, where the electromagnetic system was characterized by a uniform flat and broader frequency response, which will be observed in reference to FIG. 18. While the normal human ear has perception of sound in the 20–20,000 Hz range, the critical speech range is 500–3000 Hz. Based on this data, the electromagnetic principle was used for the present invention.

EXPERIMENTAL TESTS

Two versions of middle ear stimulator using the electromagnetic principle were developed: (1) miniaturized driving coil (2.25 mm diameter) by 13.5 mm long (1300 turns of AWG #45 copper wire) and a cup-like samarium cobalt magnet ($SmCO_5$); (2) special fine diaphragm or metal membrane, 6 mm in diameter excited by electromagnetic components. A 5-0 stainless steel wire was soldered to the center of the metal membrane to be crimped to the ossicles. For comparison, a piezoelectric stimulator of bimorph design attached to the head of the stapes was also evaluated in the laboratory. The electromagnetic coil with the magnet on the head of the stapes was found overall to be more efficient and have more advantages. The systems were tested in fresh human cadavers and fresh cat cadavers.

Ossicular microvibration below one micron was measured using an optoelectronic laser beam system. The displacement of the stapes or incus in the middle ear of fresh cat cadaver (less than 8 hours after death) was measured in response to the activation of the different types of implantable middle ear hearing aid. Also, the characteristics of the two types of electromagnetic stimulators and the piezoelectric stimulator driving the isolated stapes of anesthetized cats were compared. The electromagnetic stimulator has a more uniform flat and broader frequency response and does not require direct contact with the stapes. The results were similar to the data shown in FIG. 18.

For these reasons, the electromagnetic miniaturized driving coil was selected after the preliminary engineering testing to be used in acute animal experiments. Seven anesthetized adult cats were used. The preoperative hearing thresholds to 100 micro sec rarefaction clicks were recorded using a Nicolet Compact IV electrodiagnostic unit.

The skin and muscles overlying the cat's attic and bulla tympani were incised and retracted through a posterior auricular approach. With the aid of the Zeiss operating microscope, an atticotomy was performed using an electric drill with cutting burs and bone curettes. The incus was then removed and the hearing again tested after the atticotomy defect was sealed with bone wax. A small cylindrical $SmCO_5$ magnet (27 mg), cup-shaped was placed over the head of the stapes. A central portion had been drilled out from one end of the magnet so that the head of the stapes could fit into the magnet.

Cyanoacrylate was used to cement the magnet to the stapes using nonmagnetic instruments. Care was taken to keep the middle ear dry and to assure that the magnet was able to vibrate freely and did not abut any other part of the middle ear cavity, the malleus, or the facial nerve.

A silicone-coated ferrite core transducer coil (13.5 mm length×2.25 mm diameter) with AWG #45 copper wire (1300 turns) was placed approximately 2 mm from the stapes magnet assembly and held into a fixed position with external devices. The cat's head was immobilized in a vise-like device. The resistance of the coil was 118.3 Ohms.

1. ACOUSTIC MEASUREMENTS

Auditory brainstem potentials (ABP) were elicited and recorded preoperatively and postoperatively in the acute experimental animal (cat) using a Nicolet Compact IV electrodiagnostic system. The experimental measurement protocol required three different transducer interfaces: earphone/ear drum; earphone/microphone and coil/magnet as described below. An open (free-field system) was thus employed with intensities monitored on an oscilloscope at the level of the earphone by a probe microphone.

During ear drum stimulation, probe microphone measurements into the ear canal to within 5 mm of the ear drum showed a signal enhancement of no greater than 3 dB referenced to the output of the earphone and this could theoretically be offset by changing the earphone/microphone interface distance. However, the coil/magnet interface distance was more critical as variations of 1 mm could produce a threshold differential of as great as 5 to 10 dB. Therefore, signal intensities were reported in increments of no less than 5 dB to offset any uncontrolled measurement error incurred by the changing transducer interface distance.

While the anesthetized animal was secured in the stabilizing frame: (1) the TDH39P shielded earphone was placed at 2-3 cm from the ear drum or at 1 cm from the microphone of the telemetry unit or (2) the electromagnetic driving coil was placed at 2 mm from the stapedial magnet. Stimuli consisted of 100 sec. monopolar square pulses at a rate of 22.3 per second delivered either as acoustic click stimuli by the earphone or as direct current pulses to the electromagnetic driving coil. Intensities were measured from the coil voltage and current using an oscilloscope. All recordings were made in the free-field environment.

The EEG activity was recorded in a single channel bipolar derivation from Grass platinum subdermic needle electrodes applied in a midline montage: midline central scalp, neck with supraorbital site as ground. This montage remained constant for all recordings and was selected for its equidistance to either ear and for its remote location from the surgical site, minimizing interference artifact observed when the electromagnetic driving coil was in close proximity to the active recording site.

The auditory brainstem evoked response was averaged over several hundred sweeps to enhance the signal-to-noise ratio. The frequency response of the amplifier was set at 100 to 3000 Hz pass band and the averager was gated on during the 10 msec. following each stimulus presentation.

The response emerged as the classic far-field potential consisting of five characteristic peaks at higher stimulus intensities with a robust Wave IV noted in the species persisting at lower intensity levels.

In each experimental condition, a reference intensity presentation series was established and replicated at 90 dBSPL. Successive runs were then performed at 5 dB decrements until a minimal response level (ABP threshold) was bracketed and replicated. Each averaged response was analyzed for morphology and replicability.

Each animal was evaluated in one preoperative and three postoperative conditions.

Preoperative: With an earphone at the test ear and contralateral broad band masking delivered via an insert earphone, ABP was obtained to click stimuli at the reference level (90 dBSPL) which is extrapolated to 60 dBHL. ABP thresholds were established on a 5 dB increment scale and served as the threshold value against which postoperative thresholds were compared.

Postoperative #1: ABP thresholds were reestablished to adjust for changes incurred by the operative technique, (i.e., drilling, opening the bulla tympani, disruption the ossicular chain). The operative site was cleared of blood and sealed with bone wax prior to testing. As the operative technique involved removal of the incus, substantial interaural threshold differences were created, necessitating high levels of contralateral broadband masking to limit participation of the nontest ear. Masking was demonstrated to be effective provided that stimulus intensity did not exceed 100 dBSPL (70 dBHL).

Postoperative #2: The monopolar square wave current pulse from the Nicolet system was applied to the driving coil mounted to a stabilizing frame and positioned at 2 mm distance from the $SmCO_5$ magnet glued to the stapes head. ABP thresholds were then reestablished on a negative dB scale relative to the reference coil voltage and current.

Postoperative #3: In this experiment, click stimuli were then transduced by the TDH39P earphone now mounted at a distance of 1 cm to the electret condenser microphone of the telemetric radio frequency coil system. Threshold measures were again performed as described in the preoperative condition.

2. EXPERIMENTAL RESULTS

Figure 19:
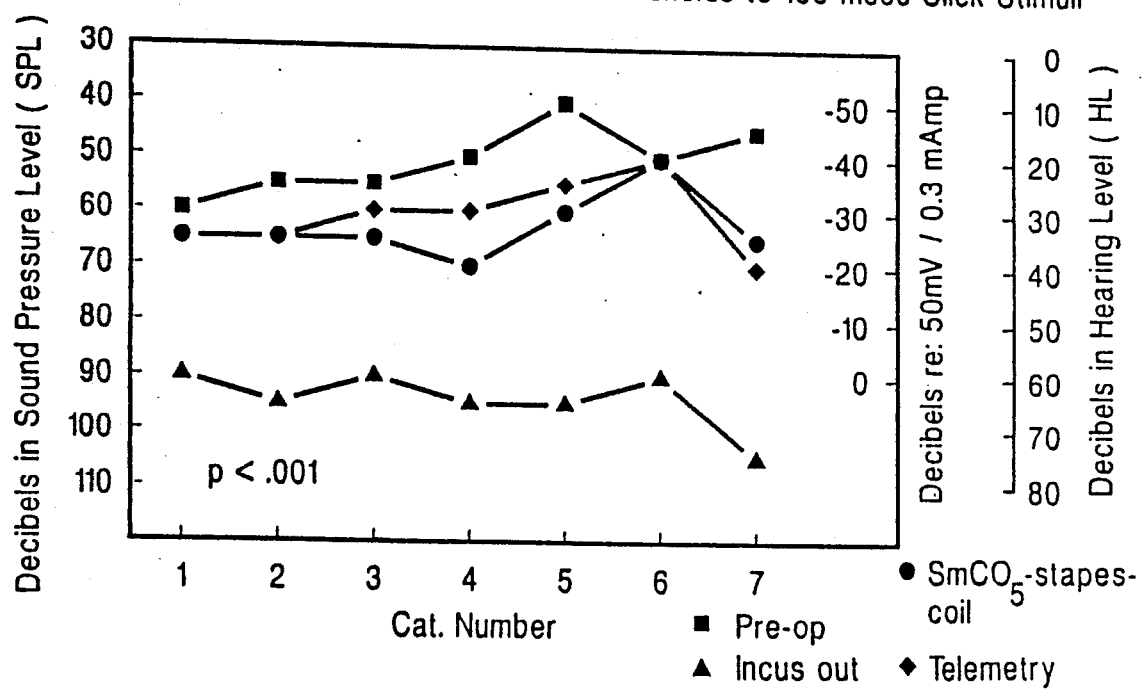
FIG. 19 shows results of tests of the partially implantable electromagnetic hearing aid which were performed in cats and in which a 35 dB gain (average) was achieved.

FIG. 19 depicts the ABP thresholds for each experimental condition in the seven acute animal experiments.

In the preoperative baseline condition, the mean ABP click thresholds in decibels sound pressure level was 50.71 dBSPL (S.D.=6.7) with a 20 dB range of values from a minimum of 40 dBSPL to a maximum of 60 dBSPL Equivalent thresholds in hearing level are 30 dB less than the sound pressure values, postoperatively, with the incus removed and the atticotomy defect sealed with bone wax, mean click threshold increased to 94.28 dBSPL (S.D.=5.34), ranging from 90 to 105 dBSPL.

In the second postoperative condition, ABP thresholds were reassessed in order to evaluate the coil/magnet interface. As described above, this measure was performed on a different scale using pulsed direct current (DC) generated by the Nicolet system with 50 mV, 0.3 mA as a reference level: 0 dB. This is the result of driving the coil with the Nicolet output set at "90 dBSPL". Coil induced thresholds ranged from $-40$ dB to $-20$ dB with a mean value of $-27.14$ dB (S.D.=6.36).

Six of the seven cat subjects were included in the third postoperative auditory measurement. In this condition, ABP click thresholds were reestablished ranging from 50 to 70 dBSPL with a mean threshold of 60 dBSPL (S.D.=7.07).

Implant gain was considered as the amount of threshold improvement achieved for each subject by means of the implanted telemetric device as compared to the baseline thresholds obtained in the surgically-altered condition, incus removed (postoperative 1). Thus, implant gain value is expressed in decibels referenced to the postoperative 1 condition. The mean "implant gain" was 35 dB (S.D.−4.47) with values ranging from 30 to 40 dB of gain.

A paired test comparing the differences in means between the surgically altered condition (postoperative #1) and the implanted condition (postoperative #3) was significant (t=19.17; df=5; p<0.001) indicating that the observed improvements in threshold with the implanted device could not be attributed to sampling error or other chance factors. The experimental data, particularly the significant improvement noted with the telemetric circuit in place, supports the original research objectives: (1) to provide sufficient acoustic gain, and (2) minimal power consumption of the implant. A mean acoustic gain of 35 dB was achieved with the telemetry unit and this can be further increased by providing additional amplification. The external unit can very well be built with a more powerful adjustable amplifier which can be controlled by the user.

The power consumption of the implanted portion of the device was efficient, consuming only 15 microwatts at 0 dB which is 27.14 decibels (mean value) above the threshold measured in this condition. This small power requirement made possible the design of the described telemetric system. The estimated power consumption of the external telemetry unit was 2.4 milliwatts (4 V, 0.6 mA). As this represents the first prototype unit, additional technological refinements in progress can be expected to decrease power consumption by a factor of three (1.3 V, 0.6 mA, 0.8 milliwatts).

This device appears to compare favorably to a medium power hearing aid with respect to acoustic gain and power requirements. With the present prototype, a 40 mA-hour battery can last for two weeks on an eight hour per day usage basis. With improved electronics, the battery life can be increased threefold. Although discrete frequency ABP thresholds were not measured in the live animal, our optoelectronic laboratory data shows a broad, flat frequency response from 100 to 5000 Hz (see FIG. 18). This type of frequency response is expected to provide good sound fidelity and with the added telemetry unit, can be further modified (shaped) to the specific needs of the patient, as in the conventional hearing aid.

The energy conversion system of the present invention is very efficient, due to its design. Acoustic energy picked up by the microphone is transformed into an electrical signal which is amplified and delivered directly to the transmitting (external) antenna, avoiding the need for acoustic energy conversion typical of the conventional hearing aid. The conventional hearing aid requires a second conversion of energy (electrical to acoustic) by the speaker. The acoustic energy delivered to the ear drum must be transferred through air molecules which, in turn, leads to a further depletion of energy due to impedance mismatches and conduction losses. Not only does the elimination of a speaker lead to a better conversion of energy in the system, but it also avoids the well-known problem of feedback.

The electronics of the implanted portion of the system are completely passive, simple in design, and the components are very inexpensive. They contain no transistors. They are composed of a coil, two diodes, one capacitor, and a driving electromagnetic coil with associated wiring. This implanted system requires no battery for operation. It is designed to be hermetically sealed and silicone coated. The components should last indefinitely, requiring no revision surgery for electronic malfunction. If there is a need for a battery, reoperations are not necessary for battery change. Hermetic sealing avoids corrosive interactions between the hardware and body fluids. The electromagnetic forces are transmitted to the ossicular chain on a contactless basis, therefore avoiding wear and tear of the ossicular chain.

The several embodiments can be adapted to the specific needs of the patient. Patients with motivation and good manual dexterity, required for insertion and care, can utilize the embodiments employing the outer ear canal units 32, 52, and variations thereof. Older patients, especially those with limited manual dexterity would be candidates for the miniaturized partially hidden, partially implanted hearing aid embodiment of FIG. 15, and variations thereof. Either of these variations provides simplicity in electronics and excellent cosmetic advantages. Should the outer ear canal or external units 32 and 52, respectively, malfunction, there would be no "down time" as the patient can replace it immediately with a spare unit.

While in accordance with provisions of the statutes there are illustrated and described herein specific embodiments of the invention, those skilled in the art will understand that changes may be made in the form of the invention covered by the following claims, and that certain features of the invention may sometimes be used to advantage without a corresponding use of the other features.

I claim:

1. A partially implantable hearing device, comprising:
    a replaceable outer ear canal unit, having means for generating radio frequency waves responsive to acoustic energy received by the unit, and adapted to be located inside an outer ear canal of an ear;
    means for holding said replaceable outer ear canal unit in a selected position in the outer ear canal;
    an implanted means for generating a first magnetic field responsive to said radio frequency waves, wherein said means for generating the first magnetic field comprises an internal induction coil implanted under the skin in the outer ear canal wall for transcutaneously receiving said radio frequency waves from said radio frequency waves generating means, an electromagnetic driving coil connected to said internal induction coil for generating said first magnetic field responsive to said radio frequency waves, and means for positioning said electromagnetic driving coil adjacent to and at a distance from an implanted magnet securely attached to the location on the bone in the ossicular chain in the ear;
    the implanted magnet having a second magnetic field located adjacent to said electromagnetic driving coil at a distance sufficient to permit the first and second magnetic field to interact with each other to cause the magnet to vibrate in a manner responsive to the acoustic energy received by the unit; and
    means for securely attaching the implanted magnet to a location on a bone in the ossicular chain in the ear.

2. The hearing device of claim 1, wherein the means for generating the radio frequency waves responsive to acoustic energy received by the unit comprises:
    means for converting the acoustic energy received by the unit into electrical signals representative thereof;
    means for amplifying the electrical signals;
    means for providing electrical energy to the converting and amplifying means; and
    an external induction coil, connected to said amplifying means, for generating the radio frequency waves responsive to the acoustic energy received by the unit.

3. The hearing device of claim 2, wherein the means for converting the acoustic energy received by the unit into electrical signals representative thereof comprises electret microphone.

4. The hearing device of claim 3, wherein the electret microphone is located facing the ear associated with the outer ear canal which receives the unit.

5. The hearing aid of claim 2, wherein the means for holding the replaceable outer ear canal unit at the selected position in the outer ear canal comprises:

an external positioning magnet, located in the replaceable outer ear canal unit near an outer surface thereof; and an internal positioning magnet, implanted under the skin in the outer ear canal wall, for interacting with and holding the external positioning magnet and its attached unit at the selected position in the outer ear canal.

6. The hearing device of claim 5, wherein the external induction coil is substantially adjacent to the internal induction coil implanted under the skin in the outer ear canal wall when the internal and external positioning magnets are holding the unit at the selected position in the outer ear canal wall.

7. The hearing device of claim 6, wherein the internal and external positioning magnets are the rare earth samarium cobalt magnets.

8. The hearing device of claim 1, wherein the location on the bone in the ossicular chain in the ear is a head of a stapes bone.

9. The hearing device of claim 8, wherein the means for positioning the electromagnetic driving coil adjacent to the magnet comprises:

a titanium, L-shaped plate supporting shaft implanted and secured at one end thereof to the electromagnetic driving coil; and a hanger, located intermediate the ends of the L-shaped plate shaft and secured to the temporal bone structure.

10. The hearing device of claim 9, wherein the L-shaped plate shaft has means for telescoping to increase or decrease its length to permit selection of the optimal coupling distance between the electromagnetic driving coil and the implanted magnet attached to the head of the stapes.

11. The hearing device of claim 8, wherein the means for securely attaching the implanted magnet to the head of the stapes bone in the ossicular chain in the ear comprises:

a biocompatible, plastipore cup glued at one end to the head of the stapes bone and glued at the other end to the implanted magnet.

12. The hearing device of claim 1, wherein the electromagnetic driving coil includes a ferrite-alloy core wrapped with approximately 2000 turns of AWG #45 copper wire.

13. The hearing device of claim 12, wherein the distance between the electromagnetic driving coil and the implanted magnet is approximately 2 millimeters.

14. The hearing device of claim 13, wherein the implanted magnet is a rare earth samarium cobalt magnet.

15. The hearing device of claim 1, wherein the bone in the ossicular chain in the ear is the incus bone, where said incus bone further includes a man-made minicavity therein, and wherein the means for securely attaching the implanted magnet to the incus bone is a titanium dish connected to a T shaped titanium pin and cemented to the body of the incus.

16. The hearing device of claim 1, wherein the radio frequency waves are of the amplitude modulation (AM) radio frequency type.

17. The hearing device of claim 11, wherein the bone in the ossicular chain in the ear is the incus bone, wherein said securely attaching means includes means for vibrating said incus bone in the ear in a manner responsive to the acoustic energy received by the unit.

18. The hearing device of claim 17 further comprises a remote control unit for said vibrating means, wherein said remote control unit having remote volume control and remote power on and off control.

19. A partially implantable hearing device, comprising:

a replaceable hidden external unit, having means for generating radio frequency waves responsive to acoustic energy received by the unit, and adapted to be located externally and medially to an upper portion of a pinna of an ear;

means for holding said replaceable hidden external unit in a selected external position located medically near the upper portion of the pinna of the ear;

an implanted means for generating a first magnetic field responsive to said radio frequency waves, wherein said means for generating the first magnetic field comprises an internal induction coil implanted under a retroauricular skin behind the ear for transcutaneously receiving said radio frequency waves from said radio frequency waves generating means, an electromagnetic driving coil connected to said internal induction coil for generating said first magnetic field responsive to said radio frequency waves, and means for positioning said electromagnetic driving coil adjacent to and at a distance from an implanted magnet securely attached to the location on the bone in the ossicular chain in the ear;

the implanted magnet, having a second magnetic field, located adjacent to said electromagnetic driving coil at a distance sufficient to permit the first and second magnetic field to interact with each other to cause the magnet to vibrate in a manner responsive to the acoustic energy received by the unit; and means for securely attaching the implanted magnet to a location on a bone in the ossicular chain in the ear.

20. The hearing device of claim 19, wherein the bone in the ossicular chain in the ear is the incus bone, wherein said securely attaching means includes means for vibrating said incus bone in the ear in a manner responsive to the acoustic energy received by the unit.

* * * * *